US008684599B2

(12) United States Patent
Seppälä et al.

(10) Patent No.: US 8,684,599 B2
(45) Date of Patent: Apr. 1, 2014

(54) MEDICAL X-RAY IMAGING APPARATUS

(75) Inventors: Lauri Seppälä, Helsinki (FI); Tapio Laukkanen, Espoo (FI); Pentti Hyvärinen, Helsinki (FI)

(73) Assignee: Planmed Oy, Helsinki (FI)

( * ) Notice: Subject to any disclaimer, the term of this patent is extended or adjusted under 35 U.S.C. 154(b) by 0 days.

(21) Appl. No.: 13/643,602

(22) PCT Filed: Apr. 28, 2011

(86) PCT No.: PCT/FI2011/050387
§ 371 (c)(1),
(2), (4) Date: Oct. 26, 2012

(87) PCT Pub. No.: WO2011/135186
PCT Pub. Date: Nov. 3, 2011

(65) Prior Publication Data
US 2013/0039456 A1    Feb. 14, 2013

(30) Foreign Application Priority Data

Apr. 29, 2010 (FI) .................................... 20100180

(51) Int. Cl.
*H05G 1/02* (2006.01)
*H05G 1/04* (2006.01)

(52) U.S. Cl.
USPC .............................. 378/197; 378/15; 378/195

(58) Field of Classification Search
USPC ........ 378/4–20, 193–198, 204, 205, 208, 210
See application file for complete search history.

(56) References Cited

U.S. PATENT DOCUMENTS

| 7,108,421 B2 | 9/2006 | Gregerson et al. |
| 7,388,941 B2 | 6/2008 | Sukovic et al. |
| 7,490,982 B2 | 2/2009 | Gregerson et al. |
| 2004/0022350 A1 | 2/2004 | Gregerson et al. |
| 2008/0212743 A1 | 9/2008 | Gregerson et al. |
| 2012/0078300 A1 | 3/2012 | Mayer et al. |

FOREIGN PATENT DOCUMENTS

| DE | 101 46 915 | 7/2005 |
| EP | 1 899 234 B1 | 3/2008 |
| EP | 1 958 663 | 8/2008 |
| WO | 03/070101 A1 | 8/2003 |
| WO | 20060119420 A1 | 11/2006 |

*Primary Examiner* — Anastasia Midkiff
(74) *Attorney, Agent, or Firm* — Fay Sharpe LLP

(57) ABSTRACT

The invention relates to a medical x-ray imaging apparatus which includes a support construction (1) supporting a substantially ring-shaped structure (2), an O-arm (2), which in turn supports imaging means (21, 22) and which O-arm (2) is arranged with an examination opening (4). The imaging means (21, 22) are arranged movable within the O-arm (2). The cross-section of an outer cover (3) of the O-arm (2) in a direction perpendicular with respect to the central axis of the O-arm is arranged for its predominant portion substantially of the shape of an arch of a circle but to comprise a cut, within the sector covered by which cut the distance from the center of said arch of the circle to the edge of the outer cover (3) is shorter than within the portion of the outer cover (3) being substantially of the shape of an arch of a circle.

17 Claims, 2 Drawing Sheets

MEDICAL X-RAY IMAGING APPARATUS

FIELD OF INVENTION

The invention relates to a medical x-ray imaging apparatus according to the preamble of claim 1.

BACKGROUND OF INVENTION

Conventional apparatuses employed in medical x-ray imaging most simple of their basic structure comprise a source of radiation which is used together with a film cassette separate from the source of radiation. Hospitals commonly use also the so-called C-arch x-ray apparatuses where the source of radiation and the receiver of image information are arranged at the opposite ends of the arched arm part. Conventionally, a device group of its own consists of large-size and extremely expensive computed tomography apparatuses where the patient is typically positioned for imaging in the recumbent position within a ring-shaped or tubular structure.

Computed tomography apparatuses have also been developed into more lightweight versions. As an example of prior art arrangements, we refer to U.S. Pat. Nos. 7,108,421 and 7,388,941. In such apparatuses, imaging means rotatable for 360 degrees around the imaging station are arranged within a ring-shaped O-arm supported from the side. The O-arm may be arranged adjustable for its height position and turnable with respect to a horizontal axis.

As conventional computed tomography apparatuses have been quite massive and expensive, acquiring them e.g. for the use of hospital emergency rooms has not been possible in practice. On the other hand, it is also typical for commercial computed tomography apparatuses that they are not necessarily designed for imaging some specific anatomy or anatomies but they are more or less general imaging apparatuses. If e.g. desiring to image the patient's whole torso, the imaging station to be arranged to the apparatus as well as other dimensions of the apparatus have had to be implemented in respective proportions.

BRIEF DESCRIPTION OF INVENTION

The object of the present invention is to advance the state of the art concerning x-ray imaging apparatuses less expensive and of smaller size as compared to the conventional computed tomography apparatuses. The embodiments of the invention preferably offer a possibility to implement a cone-beam computed tomography imaging apparatus particularly designed applicable for imaging extremities, for example, the properties and price of which could bring purchase of the apparatus within resources available for e.g. emergency clinics. As the conventional computed tomography employs a narrow fan-like beam, in cone-beam tomography the beam is collimated to be genuinely two-dimensional but often to cover only a quite small specific area (volume) of the object being imaged. A special object of the invention is to advance development particularly in the field of x-ray imaging apparatuses comprising a ring-shaped arm part of the above-described type.

Especially, the object of the invention is an arrangement which can facilitate patient positioning e.g. in connection with imaging lower extremities in the horizontal position, but also in the standing position.

The object of the preferable embodiments of the invention is also an arrangement which, among others, facilitates positioning of a large or plastered foot to an examination opening of the ring-shaped arm part and further an arrangement which, among others, facilitates imaging of a patient's leg in the standing position and on the other hand, among others, improves transferability of the apparatus from one place to another. Additionally, preferable embodiments of the invention aim both at improving patient safety and, among others, offering various possibilities for installing the apparatus to facilitate installation of the apparatus at different installation sites.

Essential characteristics of the invention are described in the accompanying patent claims. Especially essential for the invention is a cut arranged to the outer cover of the ring-shaped so-called O-arm of the above-described type, which cut partially breaks the circular shape. Considering the O-arm in the vertical orientation, the cut enables, among others, driving of the examination opening of the O-arm closer to the floor level than what would be possible without such cut. On the other hand, this cut facilitates stepping over the side of the O-arm turned into the horizontal orientation, both into the examination opening of the O-arm and out of the examination opening.

Next, the invention and its preferable embodiments will be described in more detail also with reference to the enclosed figures.

DETAILED DESCRIPTION OF INVENTION

In the following, the terms centre and central axis will be used in connection with structures which do not necessarily form a true, full circle but are of circular shape only for their prevailing part. To avoid ambiguity, these terms refer in connection with this specification to a point and an axis which would be the centre or central axis of the structure in question in case that structure would form a full circle.

Furthermore, concerning one component of the apparatus according to the invention, this specification employs terms a substantially ring-shaped structure and an O-arm. When the dimension in the direction of the central axis of this structure can be significantly large with respect to the diameter of the ring-shaped structure in question, for the avoidance of doubt it is stated that in the following, vertical position of the O-arm refers to a position where the central axis of the O-arm is horizontally oriented and horizontal position of the O-arm refers to a position where its central axis is vertically oriented.

Figure 1:
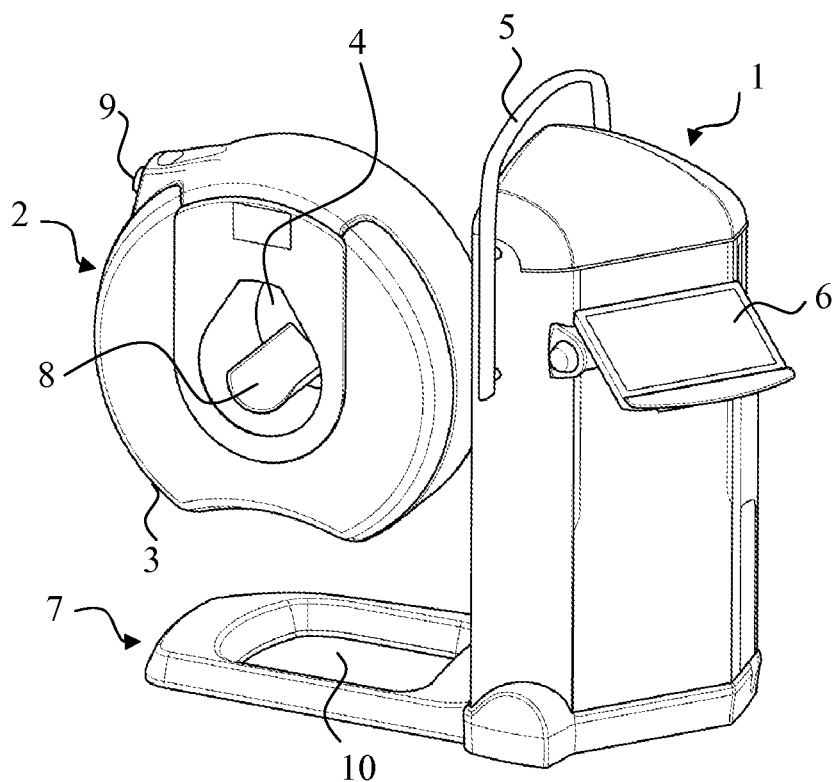
FIG. 1 shows a general view of one imaging apparatus according to the invention, its basic structure including a support construction and a substantially ring-shaped O-arm.

FIG. 1 shows a general view of one imaging apparatus according to the invention. The basic structure of the apparatus includes a support construction (1) which supports a substantially ring-shaped structure (2) within which imaging means (21, 22) of the apparatus are located and which is also referred to as an O-arm in this context. This O-arm (2) is arranged with an examination opening (4) within which an anatomy to be imaged is positioned. FIG. 1 further shows a patient support rail (5) arranged to the support construction (1), a user interface (6) being in functional connection with a control system of the apparatus, a possibly detachably attached pedestal or base part (7) projecting substantially in the direction of the O-arm, and a positioning support (8) arranged to the examination opening (4).

Mounting of the structure (2) supporting the imaging means to the support construction (1) can be arranged to enable adjustment of the height position of the O-arm (2). Furthermore, this O-arm (2) can be arranged to be turnable in at least one direction for at least 90 degrees from the vertical position shown in FIG. (1) to the horizontal position. The control of these manoeuvres can be arranged implementable aside from the user interface (6) also by means of a joy stick (9) arranged into connection with the O-arm (2) and/or the support frame (1).

When looking at the cross-section perpendicular to the direction of the central axis of the O-arm (2) shown in FIG. 1, i.e. the radial cross-section of the O-arm (2), an outer cover (3) of the O-arm (2) forms for its prevailing part a circle which yet comprises a sector where the distance from the centre of said circle to the edges of the outer cover (3) is smaller than the radius of that portion being circular for its prevailing part. In the embodiment of the invention according to FIG. 1, the part in said sector being cut off the O-arm (2) is evenly curved in the opposite direction with respect to the arch of the circle of the prevailing portion of the outer cover (3), but this cut part can also be of some other shape, such as wedge-shaped, rectangular, straight or even curved in the same direction as the portion of the arch of the outer cover (3) substantially of the shape of a circle.

When a sector of the kind described above is arranged at a section of the O-arm (2) substantially orienting downwards or being orientable downwards, it can be easier to implement e.g. imaging of lower extremities in sitting position when thanks to the invention, the examination opening (4) can be driven closer to the floor level as compared to an O-arm (2) not comprising such a cut. On the other hand, if the imaging apparatus is provided with a possibility to adjust the height position of the O-arm (2) and to turn the O-arm (2) to a position where the central axis of the O-arm (2) is substantially vertical, one may use the apparatus to image the patient in a standing position, too. Then, said cut arranged to the O-arm (2) makes it easier for the patient to step into the examination opening (4) and out of the examination opening as the length of the step one needs to take over the 'doorstep' formed by the O-arm (2) will be shorter.

In the embodiment of the invention according to FIG. 1, also the examination opening (4) is implemented only for its prevailing part substantially as a circle. A sector has been arranged to the examination opening (4) which forms an extension to the circle. That is, the examination opening (4) is provided with a sector in the area of which the distance of the edge of the examination opening (4) from the centre of the circular portion of the examination opening (4) (or from the central axis of the O-arm (2)) is longer than the radius of the circular portion of the examination opening (4). Such design of the examination opening (4) is preferable e.g. when the aim is to realize dimensions of the cross-section perpendicular with respect to the central axis of the O-arm structure as small as possible, such as when considering an embodiment basically designed for imaging anatomies having a smaller diameter than the diameter of the human torso, such as extremities.

Enlarging the examination opening (4) in some sector of the circle facilitates patient positioning e.g. when imaging a plastered leg. In such an embodiment of the invention we are talking about an examination opening (4) the diameter of the portion of the shape of an arch of a circle of which is e.g. of the order of 30-35 cm. In the preferable embodiment of the invention according to FIG. 1, the examination opening (4) is substantially of the shape of a droplet, i.e. the shape of its extension is substantially an equilateral triangle having a truncated apex, but said extension can naturally be of some other shape as well.

The above-described shape of the examination opening (4) differing from the circular shape is a part of one preferable embodiment of the invention, but the examination opening (4) can also be implemented in some other shape.

Figure 2:
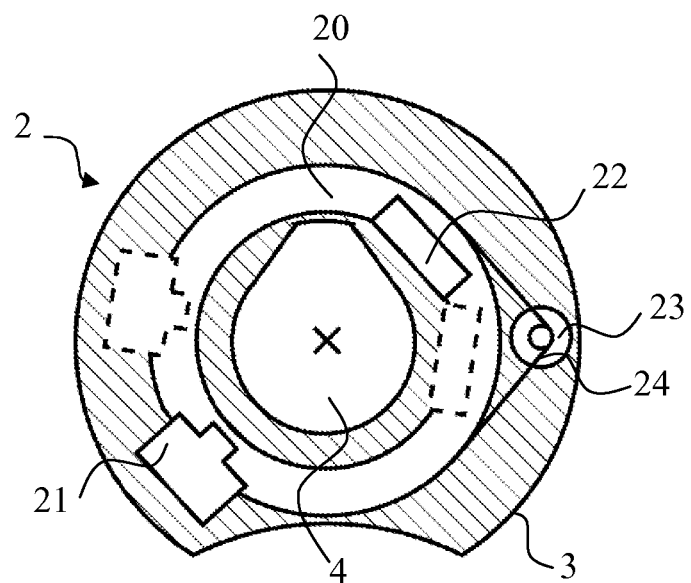
FIG. 2 shows one arrangement according to the invention for arranging imaging means to the ring-shaped imaging part.

According to the basic structure of the apparatus according to the invention, the imaging means, i.e. a source of radiation (21) and a receiver of image information (22), are arranged within the substantially ring-shaped structure (2) supporting the imaging means and as movable along a curved path within said structure, substantially on opposite sides of the examination opening (4), whereby the distance between the edge of the examination opening (4) and the outer cover (3) of the O-arm (2) (or the radial dimension of the ring of the O-arm) must naturally be arranged of adequate size to enable said paths. FIG. 2 shows a possible embodiment of the invention which includes an ring-shaped support part (20) arranged within the O-arm (2), whereto substantially on opposite sides from each other are arranged the source of radiation (21) and the receiver of image information (22). The support part (20) is arranged rotatable within the structure (2) supporting the imaging means by means of an actuator (23) and a transmission belt (24). Hence, it is possible to image the object positioned at the examination opening (4) from different directions within the range of the angle of rotation of the imaging means and to create of thus acquired image information a voxel model by means of image-data processing methods known as such.

In one preferable embodiment of the invention according to FIG. 2, the source of radiation (21) and the receiver of image information (22) are arranged movable within said substantially ring-shaped structure (2) supporting the imaging means with respect to a centre of rotation such that the source of radiation (21) (the focus of the source of radiation) moves at a different distance from said centre of rotation than the receiver of image information (22). In the arrangement according to FIG. 2, the source of radiation (21) is attached on the outer circumference of the ring-shaped support part (20) whereby, when rotating the support part (20), the focus of the source of radiation (21) moves farther from said centre of rotation than the receiver of image information (22) attached on the side of the inner circumference of the support part (20). When the receiver of image information (22) is thus brought closer to the volume being imaged, it is possible when using a detector (22) of given size to use a wider beam and thus increase the volume being imageable as compared to that the receiver of image information (22) were to move farther from the object.

According to one preferable embodiment of the invention, the range of movement of the imaging means is implemented unlike in some prior-art apparatuses of similar type, i.e. by arranging the source of radiation (21) and the receiver of image information (22) movable along a curved path substantially on opposite sides of the examination opening (4) for a shorter distance than 360 degrees. This distance is referred to in the context of this specification as an angle of rotation, and preferably it is arranged to be somewhat larger than 180 degrees but then substantially smaller than 360 degrees, such as of the order of 210+/−20 degrees. Then, arranging the imaging means (21, 22) to be movable at different distances from the centre of rotation may preferably be implemented particularly in an arrangement comprising the above-described cut in the O-arm (2) and extension in the examination opening (4). The range of manoeuvring of the source of radiation (21) can be arranged not to extend to that sector of the O-arm in which the outer cover (3) has been cut like described above and, on the other hand, the range of manoeuvring of the receiver of image information (22) not to extend to that sector of the O-arm (2) in which is arranged an extension of the examination opening (4) as described above. When the utmost dimensions of said extension and cut from the centre of rotation of the imaging means are arranged appropriate with respect to those different distances at which the imaging means are rotated from the centre of rotation, the apparatus can be implemented as shown in FIG. 3 such that the source of radiation (21) arranged to move farther from the centre of rotation is able to move outside the extension of the examination opening (4) and the receiver of image information (22), again, inside the cut arranged to the outer cover (3) of the O-arm (2).

Especially, such embodiment of the invention enables a structure where, e.g. considering imaging of extremities, due to the extension arranged to the examination opening (4) it is possible to implement the diameter of the circular portion of the examination opening (4) smaller than would be possible without the extension sector and, further, it is possible to arrange the cut to the outer cover (3) of the O-arm (2) which facilitates several positioning procedures of a patient. Such an embodiment of the invention is implementable as a compact structure and it enables realizing both the examination opening (4) and the outer dimensions of the whole O-arm (2) smaller than would otherwise be possible.

It was mentioned above that the extension arranged to the examination opening (4) facilitates e.g. positioning of a plastered leg to the examination opening. Placing the anatomy to be imaged to the examination opening (4) can be further facilitated by arranging the patient positioning support (8) arranged in connection with the examination opening (4) movable or detachably attached such that it is both positionable to a desired location within the examination opening (4) for imaging and positionable or transferrable to a place where it impedes patient positioning as little as possible. The purpose of such patient positioning support (8) is to assist positioning of the anatomy being imaged to a desired point with respect to the O-arm (2). Preferably, the patient positioning support (8) comprises a concave structure whereto an upper or a lower extremity can be positioned for the duration of the imaging.

The angle of rotation of the imaging means (21, 22) described above is sufficient in cone-beam tomography, in which the beam generated by the source of radiation (21) is arranged to be limited to a true two-dimensional beam and the receiver of image information (22), again, of its form and dimensions at least such that it covers said two-dimensional beam. In the apparatus according to the invention, such beam can also be arranged to be limited to more than one size and/or shape, whereby the receiver of image information (22) must naturally be arranged either to cover all possible beam sizes and shapes or it must be arranged changeable.

The patient support rail (5) of the imaging apparatus shown in FIG. 1 is preferably arranged to extend from top of the support construction (1) substantially to at least one side of the support construction, especially to a side from the direction of which the patient is at least primarily thought to station oneself for imaging—i.e. preferably to the side in the direction of which the cut of the outer cover (3) of the O-arm (2) is arranged to be turned. The patient support rail (5) especially facilitates imaging in standing position, i.e. imagings where the O-arm (2) is turned into a position where its central axis is in the vertical orientation, when the patient can take support for himself/herself from the rail (5) when standing inside the O-arm (2) as well as when stepping in and out of it. In a preferable embodiment of the invention, the patient support rail (5) extends to at least one such side of the support construction (1) in the direction of which the cut sector arranged to the O-arm (2) is arranged to be turned.

The projecting base part (7) arranged attachable into connection with the support construction (1) shown in FIG. 1 can be a component optionally arranged to the apparatus and its use is advantageous particularly when there is no intention to bolt or otherwise mount the support construction (1) on the floor, or if the location where the apparatus is considered to be used does not enable floor mounting. The projecting base part (7) assists the apparatus staying upright and, at the same time, it is e.g. possible to arrange wheels under the projecting base part (7) and the support construction (1) to facilitate transfer of the apparatus, such as transferring it from one imaging room to another. Considering these various possible ways to install the apparatus, it is preferable to arrange the projecting base part (7) detachably attachable to the support construction (1) of the apparatus.

In the embodiment of the invention according to FIG. 1, an opening (10) located substantially below the O-arm (2) has been arranged to the projecting base part (7). The purpose is that this opening (10) shall locate at a point where the patient being imaged in standing position stands during the imaging, i.e. substantially at the point of the examination opening (4) of the O-arm (2) when it is turned into a position where the central axis of the O-arm (2) is oriented vertically. When the patient stands in such an opening (10) of the projecting base part (7) and not on top of the projecting base part (7), first, it minimises the risk of the patient's foot getting squeezed between the O-arm (2) and the projecting base part (7). Second, stepping from a floor to the floor is easier and safer as compared to stepping up onto a plane located higher with respect to the floor level, or stepping down from there. Furthermore, when the apparatus can be considered to be delivered to the client either as to be fixedly mounted on the floor without the projecting base part (7) or together with it, such a projecting part arrangement provides the advantage that the patient's leg being imaged in the standing position is always at the same level with respect to the apparatus irrespective whether the projecting base part (7) is being used or not. Hence, e.g. the basic settings of the operation modes of the apparatus considering the height position of the O-arm (2) used in the imagings can be the same irrespective of whether the apparatus is installed as mounted to the floor or with the projecting base part (7). Furthermore, if one e.g. has to use a stand on which the patient steps in order to bring an ankle high enough for imaging, even then one only needs a single size stand, and the imaging height with respect to the floor level is also in this case the same in both types of installation of the apparatus.

The opening (10) arranged to the projecting base part (7) can be of any shape and even open in the direction of any edge of the projecting base part (7). What is important is that at least part of the opening (10) is located at a point whereto the patient steps and where the patient stands when the imaging is being realised and the O-arm being turned to a position where orientation of its central axis is essentially vertical.

Figure 3A:
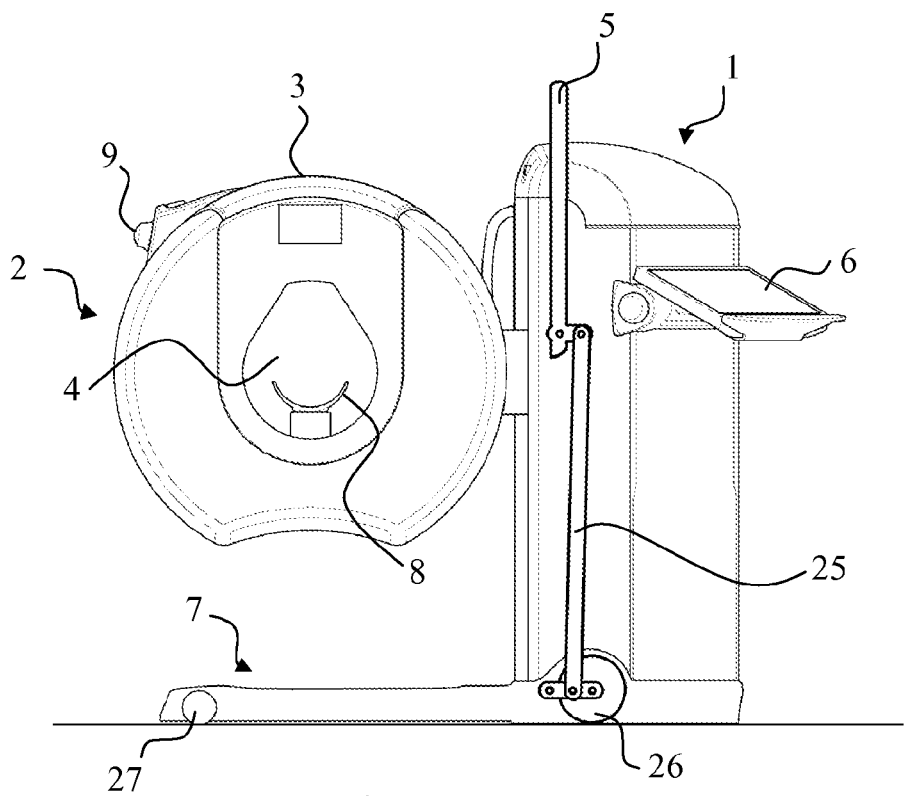
FIGS. 3a and 3b show an embodiment of the invention where the apparatus is arranged with a patient support rail, for which at least one other function than the patient support function has been arranged.
Figure 3B:
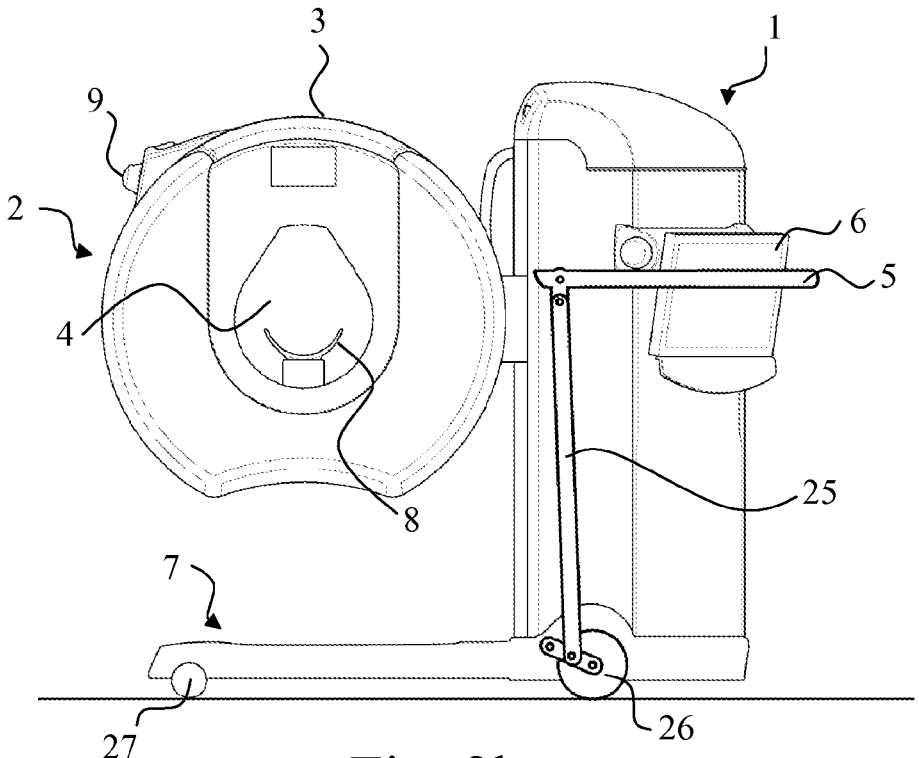

In one preferable embodiment of the invention, the patient support rail (5) can be arranged multifunctional. FIGS. 3a and 3b show how the patient support rail (5) is arranged turnable over the support construction (1) from the vertical position to the horizontal position, in the direction away from the O-arm. The turning, and locking of the rail (5) to the horizontal position can be implemented such that the manoeuvre in question simultaneously lifts the support construction (1) up from the floor by means of a mechanism (25) arranged into connection with the rail (5), which mechanism (25) pushes wheels (26) arranged below the apparatus downwards. Returning the patient support rail (5) to the upper position lifts the wheels (26) back up. It is also possible to arrange below the projecting base part (7) a wheel or wheels (27), the lowering and lifting of which can be arranged to take place together with the wheels (26) arranged below the support construction (1), or with its own mechanism. One alternative is to implement the wheel or wheels (27) of the projecting base part (7) as a fixed structure and to arrange the projecting base part (7) liftable higher when starting to transfer the apparatus from one place to another.

In the arrangement of the kind described above, the patient support rail (5) can be used in addition to a support rail also as a push bar when transferring the apparatus from one place to another and, at the same time, it functions as protection for the user interface or control panel (6) arranged into connection with the support construction (1) when transferring the apparatus. Thus, the patient support rail (5) in fact becomes a multifunctional rail: the multifunctional rail operates as use-mode alternator of the apparatus when changing the apparatus from one standing on the floor to one transferable, and vice versa, the rail protects the apparatus during the transfer of the apparatus and, offers support for the patient in connection with imaging. Concerning the mechanism 25, it is easy to attach thereto a brake feature and a possibility to increase ground clearance e.g. for crossing doorsills.

In the embodiment according to FIG. 1, the user interface of the apparatus is also in functional connection with the joy stick (9) arranged in connection with the O-arm (2). The ergonomic positioning of this joy stick (9) enables moving the O-arm (2) without the need for one to move away from the immediate proximity of the O-arm (2), and thus also from the patient. Preferably, the joy stick (9) is arranged to operate at least such that moving it downwards moves the O-arm (2) downwards and moving it upwards moves the O-arm (2) upwards.

The preferable embodiment of the invention shown in FIG. 1 can be implemented as a relatively compact structure and, for achieving many of the advantages described above, as a structure where the radius of the prevailing portion of the examination opening (4) being of the shape of an arch of a circle is of the order of 15 cm or slightly more and, on the other hand, the radius of the prevailing portion of the O-arm (2) of the shape of an arch of a circle is of the order of 50 cm or even less. Here, the distance of the focus of the source of radiation (21) from the centre of rotation of the imaging means (21, 22) can preferably be arranged e.g. for about 390 mm and that of the receiver of image information for about 190 mm.

It is obvious for one skilled in the art that as for its details, the present invention may be implemented also in other ways than according to the embodiments of the invention described above.

The invention claimed is:

1. A medical x-ray imaging apparatus, which apparatus includes
    a support construction which is arranged to support a substantially ring-shaped structure supporting imaging means, which imaging means include a source of radiation and a receiver of image information, which imaging means are arranged within said substantially ring-shaped structure supporting the imaging means substantially on opposite sides of each other and movable within said ring-shaped structure supporting the imaging means,
    which apparatus includes in said ring-shaped structure supporting the imaging means an examination opening wherein the object to be imaged is positionable for imaging,
    and in which apparatus said substantially ring-shaped structure supporting the imaging means is arranged movable with respect to said support construction at least in the vertical direction and, on the other hand, turnable with respect to an axis substantially parallel with the horizontal diagonal of a radial cross-section of the ring-shaped structure in question, characterized in that
    said substantially ring-shaped structure supporting the imaging means includes an outer cover the cross-section of which in a direction perpendicular with respect to the central axis of said ring-shaped structure is for its prevailing portion arranged substantially of the shape of an arch of a circle but to comprise a cut, and within the sector covered by the cut the distance from the centre of said arch of a circle to the edge of the outer cover is shorter than within said portion of the outer cover substantially of the shape of an arch of a circle.

2. An imaging apparatus according to claim 1, characterized in that said cut is substantially evenly curved in the direction opposite to said portion of the outer cover which for its prevailing portion is substantially of the shape of an arch of a circle.

3. An imaging apparatus according to claim 1, characterized in that said source of radiation and receiver of image information are arranged movable within said substantially ring-shaped structure supporting the imaging means with respect to a centre of rotation for an angle of rotation which is wider than 180 degrees but narrower than 360 degrees.

4. An imaging apparatus according to claim 1, characterized in that said source of radiation and receiver of image information are arranged movable within said substantially ring-shaped structure supporting the imaging means with respect to a centre of rotation such that the source of radiation moves at a different distance from said centre of rotation than the receiver of image information.

5. An imaging apparatus according to claim 4, characterized in that the receiver of image information is arranged to move closer to said centre of rotation than the focus of said source of radiation.

6. An imaging apparatus according to claim 1, characterized in that within said ring-shaped structure supporting the imaging means is arranged a substantially ring-shaped support part, said source of radiation and receiver of image information are attached to that support part and said the support part is arranged rotatable within the structure supporting the imaging means.

7. An imaging apparatus according to claim 1, characterized in that said examination opening is arranged for its prevailing portion substantially of a shape of an arch of a circle but to comprise an extension, within a sector covered by which extension the distance from the centre of said arch of a circle to the edge of the examination opening is longer than within said portion of the examination opening being substantially of the shape of an arch of circle.

8. An imaging apparatus according to claim 7, characterized in that said extension of the examination opening is arranged to be located substantially on the opposite side of said ring-shaped structure supporting the imaging means than said cut of the outer cover.

9. An imaging apparatus according to claim 8, characterized in that a range of movement of said source of radiation within said ring-shaped structure supporting the imaging means is arranged not to extend to that sector of the structure supporting the imaging means wherein said cut of the outer cover has been made, and a range of movement of the receiver of image information is arranged not to extend to that sector of the structure supporting the imaging means wherein said extension of the examination opening has been arranged.

10. An imaging apparatus according to claim 7, characterized in that the outmost dimensions of said extension and cut from the centre of rotation of the imaging means are arranged such that the source of radiation arranged to move farther from the centre of rotation is able to move outside the extension of the examination opening and the receiver of image information inside the cut arranged to the outer cover of the structure supporting the imaging means.

11. An imaging apparatus according to claim 1, characterized in that a beam generated by said source of radiation is arranged to be limited to a true two-dimensional beam and, again, the receiver of image information for its form and dimensions at least such that it covers said two-dimensional beam.

12. An imaging apparatus according to claim 1, characterized in that the radius of the prevailing portion of said examination opening which is substantially of the shape of an arch of a circle is of the order of 15 cm or somewhat more, the radius of the prevailing portion of said structure supporting the imaging means which is substantially of the shape of an arch of a circle is of the order of 50 cm or less, and/or that the distance of the focus of the source of radiation from the centre of rotation of the imaging means is about 390 mm and the distance of the receiver of image information from the centre of rotation of the imaging means is about 190 mm.

13. A medical x-ray imaging apparatus, which apparatus includes
   a support construction which is arranged to support a substantially ring-shaped structure supporting imaging means, which imaging means include a source of radiation and a receiver of image information, which imaging means are arranged within said substantially ring-shaped structure supporting the imaging means substantially on opposite sides of each other and movable within said ring-shaped structure supporting the imaging means,
   which apparatus includes in said ring-shaped structure supporting the imaging means an examination opening wherein the object to be imaged is positionable for imaging,
   and in which apparatus said substantially ring-shaped structure supporting the imaging means is arranged movable with respect to said support construction at least in the vertical direction and, on the other hand, turnable with respect to an axis substantially parallel to the horizontal diagonal of a radial cross-section of the ring-shaped structure in question,
characterized in that into connection with said support construction is arranged a base part projecting in the direction of said substantially ring-shaped structure supporting the imaging means and in which is arranged an opening which is located at least partially below said examination opening when said structure supporting the imaging means is turned to a substantially horizontal position.

14. An imaging apparatus according to claim 13, characterized in that said opening is arranged at least the same size as said examination opening in the ring-shaped structure supporting the imaging means.

15. An imaging apparatus according to claim 13, characterized in that it is implemented in connection with an imaging apparatus according to any one of the claims 1-10.

16. An imaging apparatus according to claim 3, characterized in that said source of radiation and receiver of image information are arranged movable within said substantially ring-shaped structure supporting the imaging means with respect to a centre of rotation for an angle of rotation which is between 180 degrees and 230 degrees.

17. An imaging apparatus according to claim 3, characterized in that said source of radiation and receiver of image information are arranged movable within said substantially ring-shaped structure supporting the imaging means with respect to a centre of rotation for an angle of rotation which is between 180 degrees and 190 degrees.

* * * * *